United States Patent

Raizon et al.

Patent Number: 5,192,797
Date of Patent: Mar. 9, 1993

[54] DERIVATIVES OF 2-AMINOALKYL-5-ARYLALKYL-1,3-DIOXANES, THEIR PREPARATION AND THEIR THERAPEUTIC APPLICATION

[75] Inventors: Bernard Raizon, Vigneux; Yannick Evanno, Paris; Odette LeGalloudec, Morigny, all of France

[73] Assignee: Synthelabo, Paris, France

[21] Appl. No.: 714,182

[22] Filed: Jun. 14, 1991

[30] Foreign Application Priority Data

Jun. 15, 1990 [FR] France .................. 90 07483
Apr. 15, 1991 [FR] France .................. 91 04578

[51] Int. Cl.$^5$ .................. A61K 31/335; C07D 319/06
[52] U.S. Cl. ................................. 514/452; 549/373
[58] Field of Search .................. 549/373; 514/452

Primary Examiner—Nicky Chan
Attorney, Agent, or Firm—Jacobson, Price, Holman & Stern

[57] ABSTRACT

A compound which is a 2-aminoalkyl-5-arylalkyl-1,3-dioxane of general formula (I)

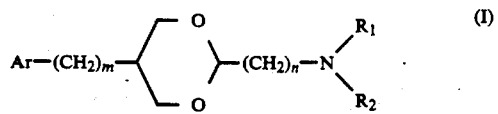

in which
 m represents 0 or 1;
 n represents 1, 2, 3 or 4;
 $R_1$ represents hydrogen or methyl;
 $R_2$ represents hydrogen, methyl or an alkanoyl group of the general formula COR' in which R' represents a hydrogen atom or a linear or branched $C_1$–$C_4$-alkyl group, or an alkoxycarbonyl group of the general formula COOR" in which R" represents a linear or branched $C_1$–$C_4$-alkyl group; and
 Ar represents either a phenyl group optionally carrying one or two substituents selected from halogen, $C_1$–$C_4$ alkyl, methoxy and trifluoromethyl, or a naphthalen-1-yl or naphthalen-2-yl group optionally carrying a substituent selected from halogen, methyl, methoxy and cyclopropylmethoxy groups,
in the form of a cis- or trans-stereoisomer, and in the form of a free base or an acid addition salt thereof and its therapeutic use.

8 Claims, No Drawings

DERIVATIVES OF 2-AMINOALKYL-5-ARYLALKYL-1,3-DIOXANES, THEIR PREPARATION AND THEIR THERAPEUTIC APPLICATION

The present invention relates to derivatives of 2-aminoalkyl-5-arylalkyl-1,3-dioxanes, their preparation and their therapeutic application.

The invention provides a compound which is a 2-aminoalkyl-5-arylalkyl-1,3-dioxane of general formula (I)

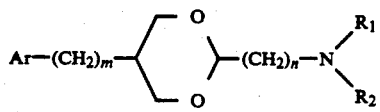

in which
m represents 0 or 1;
n represents 1, 2, 3 or 4;
$R_1$ represents hydrogen or methyl;
$R_2$ represents hydrogen, methyl, or an alkanoyl group of the general formula COR' in which R' represents a hydrogen atom or a linear or branched $C_1$-$C_4$-alkyl group, or an alkoxycarbonyl group of the general formula COOR" in which R" represents a linear or branched $C_1$-$C_4$-alkyl group; and
Ar represents either a phenyl group optionally carrying one or two substituents selected from halogen, $C_1$-$C_4$-alkyl, methoxy and trifluoromethyl, or a naphthalen-1-yl or naphthalen-2-yl group optionally carrying a substituent selected from halogen, methyl, methoxy and cyclopropylmethoxy, in the form of a cis- or trans-stereoisomer, and in the form of a free base or an acid addition salt thereof.

In a preferred embodiment of the invention, Ar represents chlorophenyl or an optionally substituted naphthalen-1-yl or naphthalen-2-yl group.

More preferably, Ar is naphthalen-1-yl optionally substituted with methoxy; n is 1 or 3; and any acid addition salt is the hydrochloride.

The invention further provides a process for the preparation of compounds of general formula (I), which comprises reacting a diol of the general formula (II)

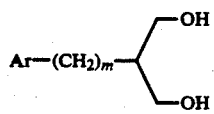

(in which m and Ar are as hereinbefore defined) with an acetal of the general formula (III)

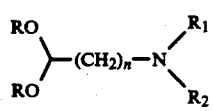

(in which n, $R_1$ and $R_2$ are as hereinbefore defined and R represents a $C_1$-$C_4$-alkyl group), which may be in the form of an acid addition salt, and if desired converting a free base of formula (I) into an acid addition salt.

The process of the invention is illustrated by the reaction scheme given below:

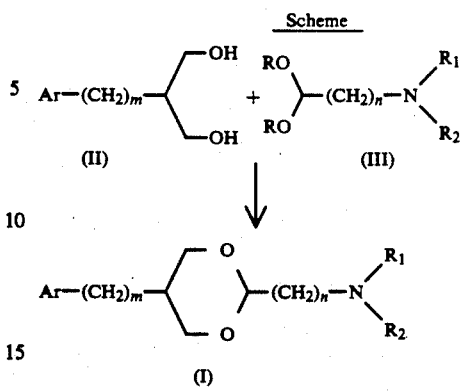

The reaction may be carried out in a solvent such as diethyl ether or benzene, at a temperature of from 20 to 80° C., depending on the solvent used, and in the presence of paratoluenesulphonic acid and/or ethereal hydrogen chloride as a catalyst.

The diols of the general formula (II) are widely described in literature and can be prepared according to known methods.

Thus, when m=0, an acid of the general formula Ar-CH$_2$-COOH can be esterified, for example, by ethanol in the presence of thionyl chloride. The resulting ester, whicih is of the general formula ArCH$_2$COOC$_2$H$_5$, can be reacted with ethyl carbonate in the presence of sodium ethoxide. Finally, the diester produced, whichis of the general formula ArCH(COOC$_2$H$_5$)$_2$, can be reduced by sodium borohydride. When Ar represents a naphthalenyl group, the ester of the general formula ArCH$_2$COOC$_2$H$_5$ can likewise be obtained starting from the corresponding 1,2,3,4-tetrahydronaphthalenone according to a process of which details are given in the examples. When m=1, a halogenated derivative of the general formula ArCH$_2$Cl can be reacted, for example, with diethyl malonate in the presence of sodium ethoxide. The diester produced, which is of the general formula ArCH$_2$CH(COOC$_2$H$_5$)$_2$ can be reduced by lithium aluminium hydride.

The acetals of the general formula (III) are also well described in the literature, and can be prepared according to known methods; thus, for example, those in the geneal formula in which at least one of $R_1$ and $R_2$ is not a hydrogen atom can be prepared starting from an amine of the general formula (III) in which $R_1$ and $R_2$ both represent a hydrogen atom, according to known methods of alkylation or of preparation of amides or carbamates.

Similar known methods can also be used to convert a compound of the general formula (I) in which $R_1$ and $R_2$ both represent a hydrogen atom into another compound in which at least one of $R_1$ and $R_2$ is not a hydrogen atom.

The following Examples illustrate in detail the preparation of some compounds according to the invention. The elemental microanalysis and the IR and NMR spectra confirm the structures of the products obtained.

The numbers given in brackets in the titles of the Examples correspond to those of the table which follows.

EXAMPLE 1

Compound No. 58

N-[5-(4-Chlorophenyl)methyl-1,3-dioxan-2-yl]methylacetamide

1.1 Diethyl 2-(4-chlorophenyl)methylpropanedioate

A solution of sodium ethoxide (2.86 g (124 mmol) of sodium in 50 ml of ethanol) is added to a solution of 20 g (124 mmol) of 1-chloro-4-(chloromethyl)benzene and 19.9 g (124 mmol) of diethylmnalonate in 50 ml of ethanol. The mixture is heated to reflux for 4 h, the solvent is evaporated under reduced pressure, and the residue is taken up with 250 ml of chloroform. The organic phase is washed with a standard solution of sodium hydrogen carbonate, dried over magnesium sulphate and evaporated, and the residue is distilled under reduced pressure (80–85° C., 4 Pa, or 0.03 mm Hg). 16.8 g (59 mmol) of product are obtained.

1.2 2-[(4-Chlorophenyl)methyl]propane-1,3-diol

A solution of 16.8 g (59 mmol) of diethyl 2-(4chlorophenyl)methylpropanedioate in 50 ml of tetrahydrofuran is added, drop by drop, to a suspension of 5 g (131 mmol) of lithium aluminium hydride in 500 ml of tetrahydrofuran. After heating to reflux for 8 h, the mixture is hydrolysed with 5 g of water, 15 g of 10% sodium hydroxide then 5 g of water, then the mixture is evaporated under reduced pressure. The residue is taken up with 200 ml of dichloromethane, the solution is washed three times with water, dried over magnesium sulphate and filtered, the filtrate is evaporated and a little diethyl ether and pentane are added to the residue. The precipitate obtained is filtered and dried in vacuo. 9.1 g (45 mmol) of product are obtained. Melting point: 58–60° C.

1.3. N-(2,2-Dimethoxyethyl)acetamide

A solution of 32 g (313 mmol) of acetic anhydride in 200 ml of benzene is added, drop by drop, to a suspension, stirred and heated to reflux, of 40 g (290 mmol) of potassium carbonate and 30 g (285 mmol) of aminoacetaldehyde dimethyl acetal in 200 ml of benzene. Reflux is maintained for 30 min., then the mixture is cooled and filtered, the precipitate is washed with benzene, the filtrate is evaporated and the residual oil is treated with vegetable charcoal in 300 ml of diethyl ether. After filtration and evaporation, 36.8 g (250 mmol) of product are obtained. $n^{25}_D = 1.4450$.

1.4. N-[5-(4-Chlorophenyl)methyl-1,3-dioxan-2-yl]methylacetamide 4 g (20 mmol) of 2-[(4-chlorophenyl)methyl]propane-1,3-diol, 2.94 g (20 mmol) of N-(2,2-dimethoxyethyl)acetamide, 0.3 g of paratoluenesulphonic acid and 4 ml of diethyl ether saturated with hydrogen chloride are added to 150 ml of diethyl ether. The mixture is evaporated in vacuo, then 150 ml of benzene are added twice to the residue, it is heated to 70–80° C. under a slight vacuum and the solvent is evaporated. The residue is cooled, 150 ml of dichloromethane are added, and the solution is washed with a saturated solution of sodium hydrogen carbonate then with water and dried over magnesium sulphate. The residue is purified twice by chromatography on a silica gel column eluted with chloroform, and it is finally recrystallised in a 70:4 mixture of cyclohexane/ethyl acetate. 1.7 g (6 mmol) of product are obtained.

Melting point: 95° C.

EXAMPLE 2

Compound No. 120

2-Aminopropyl-5-(naphthalen-1-yl)-1,3-dioxane, hydrochloride

Sufficient ethereal hydrogen chloride is added to 4 g (25 mmol) of 4,4-diethoxybutylamine in 500 ml of benzene to precipitate all the hydrochloride. 4 g (20 mmol) of 2-(naphthalen-1-yl)propane-1,3-diol in 200 ml of benzene and 100 mg of paratoluenesulphonic acid are then added, and the mixture is evaporated to dryness in a bath at 100° C. A further 700 ml of benzene are added, the mixture is evaporated under the same conditions, and the residue is then placed in vacuo at 100 C for 4 h. It is recrystallised in diethyl ether, dried at 60° C., recrystallised twice in ethanol, treating it with vegetable charcoal during the first recrystallisation, washed with diethyl ether and dried at 80° C. 3.2 g (10.4 mmol) of product are obtained.

Melting point: 191–192° C.

EXAMPLE 3

Compound No. 121

N-Methyl-2-aminopropyl-5-(naphthalen-1-yl)-1,3-dioxane, hydrochloride

3.1. N-[3-[5-(Naphthalen-1-yl)-1,3-dioxan-2-yl]propyl]-2,2,2-trifluoroacetamide 20 g (65 mmol) of 2-aminopropyl-5-(naphthalen-1-yl)-1,3-dioxane hydrochloride and 19.5 g (141 mmol) of potassium carbonate in 350 ml of benzene are heated in a Dean-Stark apparatus for 3 h. 14 g (67 mmol) of trifluoroacetic anhydride are then introduced and the mixture is heated for a further 3 h. The mixture is cooled and filtered, and the filtrate is evaporated to dryness. The residue crystallises in pentane. 15 g (41 mmol) of crude product are obtained. Melting point: 83–84° C.

3.2. N-Methyl-2-aminopropyl-5-(naphthalen-1-yl)-1,3-dioxane, hydrochloride 12 g (33 mmol) of the crude product obtained in the preceding step are dissolved in 200 ml of acetone and 20.7 g (146 mmol) of iodomethane are added, drop by drop and while stirring, and the mixture is heated to reflux. 8.2 g (146 mmol) of powdered potassium hydroxide are then added, and reflux is maintained for 15 min. The solvent is evaporated, 90 ml of water are added to the residue, and the mixture is heated to reflux for 10 min., cooled and extracted three times with ether. The ethereal phase is dried over magnesium sulphate and filtered, and sufficient diethyl ether saturated with hydrochloric acid is added to the filtrate to precipitate the hydrochloride. The latter is purified by recrystallising it twice in a 50:50 mixture of methanol/diethyl ether. After washing with diethyl ether and drying at 70° C., 6.9 g (21.4 mmol) of product are finally isolated. Melting point: 142–144° C.

EXAMPLE 4

Compound No. 123

N=[3-[5-(Naphthalen-1-yl)-1,3-dioxan-2-yl]propyl]acetamide

4.1. Ethyl naphthalene-1-acetate 100 g (537 mmol) of naphthalene-1-acetic acid in 200 ml of absolute ethanol are heated to 60° C., while stirring, and 80 ml of thionyl chloride are added slowly in such a way that reflux occurs. Reflux is maintained for 6 h, and the solvent is then evaporated under reduced pressure. The residue is taken up with 200 ml of dichloromethane, the solution is washed with a saturated solution of sodium hydrogen carbonate and then with water, dried over magnesium sulphate and filtered, and the solvent is evaporated under reduced pressure. 104 g (485 mmol) of product are obtained in the form of an oil. $n^{25}_D = 1.5800$.

4.2. Diethyl 2-(naphthalen-1-yl)propanedioate

A mixture of 103.9 g (485 mmol) of ethyl naphthalene-1-acetate and 430 ml of ethyl carbonate is stirred at 105° C., and a solution of sodium ethoxide (11 g (478 mmol) of sodium in 255 ml of absolute ethanol) is then added in such a way that the ethanol distils in the course of the introduction. The mixture is heated for a further 15 min. to distil the maximum amount of ethanol, the flask is rapidly cooled and the mixture is poured onto 300 g of crushed ice and 20 ml of concentrated hydrochloric acid. It is extracted with diethyl ether, the organic phase is dried over magnesium sulphate and filtered, and the solvent is evaporated under reduced pressure. An oil is obtained which crystallises in pentane in the cold. The crystals are separated by filtration, treated with vegetable charcoal in diethyl ether and filtered, the filtrate is evaporated and the residue is recrystallised in a 25:75 mixture of diethyl ether/pentane. 97 g (339 mmol) of crystals are obtained.

Melting point: 57–59° C.

4.3. 2-(Naphthalen-1-yl)propane-1,3-diol 50 g (175 mmol) of diethyl 2-(naphthalen-1-yl)propanedioate in 310 ml of dioxane and 300 ml of water are stirred at ambient temperature; an excess (2.2 mol, or 84 g) of sodium borohydride is then added in portions; the mixture is stirred for 8 h, and the products are left in contact for 2 days. The mixture is then hydrolysed, with stirring, while introducing crushed ice and 3N hydrochloric acid until an acidic pH is obtained. The mixture is extracted with diethyl ether, the organic phase is evaporated, and the residual oil is purified by chromatography on a silica gel column eluted with ethyl acetate. After evaporation and drying at 40° C. in the presence of phosphorus pentoxide, 18.5 g (91 mmol) of product are isolated. Melting point: 58–60° C.

4.4. N-(4,4-Diethoxybutyl)acetamide 20 g (196 mmol) of acetic anhydride in 100 ml of benzene are added, drop by drop, at reflux to a stirred suspension of 32 g (198 mmol) of 4,4-diethoxybutylamine and 24 g (174 mmol) of potassium carbonate in 600 ml of benzene. The mixture is heated to reflux for 15 min. and cooled, the precipitate is filtered and the filtrate is evaporated to dryness. The residual oil is treated with vegetable charcoal in 300 ml of diethyl ether and, after filtration and evaporation of the filtrate in vacuo, 37.3 g (183 mmol) of oily product are obtained. $n^{20}_D = 1.4472$.

4.5. N-[3-[5-Naphthalen-1-yl)-1,3-dioxan-2-yl]propyl]acetamide 10 ml of ethereal hydrogen chloride and 100 mg of paratoluenesulphonic acid are added to a mixture of 11.6 g (57 mmol) of 2-(naphthalen-1-yl)propane-1,3-diol and 11.65 g of N-(4,4-diethoxybutyl)acetamide in 300 ml of diethyl ether, and the mixture is evaporated to dryness in a bath at 50° C. 300 ml of benzene are then added twice and the mixture is evaporated to dryness in a bath at 70° C. The residue is placed in a water-jet vacuum for 45 min., the residue is taken up with 300 ml of dichloromethane, and the solution is washed with a saturated solution of sodium hydrogen carbonate and then with water. It is dried over magnesium sulphate, filtered and evaporated to dryness. The residue is recrystallised in an 80:20 mixture of ethyl acetate/dichloromethane, while treating it with vegetable charcoal. After a second recrystallisation, washing with diethyl ether and drying at 60° C, 9 g (29 mmol) of product are finally isolated. Melting point: 158–160° C.

EXAMPLE 5

Compound No. 125

Ethyl [3-[5-(naphthalen-1-yl)-1,3-dioxan-2-yl]propyl]carbamate 4 g (13 mmol) of 2-aminopropyl-5-(naphthalen-1-yl)-1,3-dioxane hydrochloride are stirred at ambient temperature for 10 min. with 4 ml of triethylamine in 200 ml of dichloromethane, 1.4 g (13 mmol) of ethyl chloroformate in 20 ml of dichloromethane are then added, drop by drop, and the mixture is stirred at ambient temperature for 3 h. Dilute hydrochloric acid is added, and the organic phase is separated, washed with water and with a saturated solution of sodium hydrogen carbonate, dried over magnesium sulphate, filtered and evaporated to dryness. An oil is obtained which crystallises in pentane; the solid is filtered and purified by chromatography on a silica gel column eluted with ethyl acetate. 2.4 g (7 mmol) of product are finally isolated.

Melting point: 93–94° C.

EXAMPLE 6

Compound No. 128

N-Methyl-N-[3-[5-(naphthalen-1-yl)-1,3-dioxan-2-yl]propyl]acetamide

A mixture of 3 g (9.3 mmol) of N-methyl-2-aminopropyl-5-(naphthalen-1-yl)-1,3-dioxane hydrochloride with 2.45 g (18 mmol) of potassium carbonate in 100 ml of benzene is heated to 60° C while stirring. 1 g (10 mmol) of acetic anhydride is added and the mixture is heated to reflux for 30 min.; it is cooled and filtered, the filtrate is washed with water, dried over magnesium sulphate and filtered and the filtrate is evaporated to dryness. The residue is taken up with diethyl ether, treated with vegetable charcoal and filtered, and the filtrate is evaporated. After drying at 50° C, 1.3 g (4 mmol) of oily product are obtained. $n^{21}_D = 1.5752$.

EXAMPLE 7

Compound No. 136

N-[5-(6-Methoxynaphthalen-1-yl)-1,3-dioxan-2-yl]methylacetamide

7.1. Ethyl 6-methoxynaphthalene-1-acetate 50 g (284 mmol) of 6-methoxy-1,2,3,4-tetrahydronaphthalen-1-one, 62 g (371 mmol) of ethyl bromoacetate, 5 g (39 mmol) of iodine and 33 g (500 mmol) of zinc powder are placed, under argon, in a 2 l reactor containing 500 ml of tetrahydrofuran, and the mixture is heated on an oil bath so as to initiate the reaction. When the temperature reaches about 50° C, the reaction starts and stirring is increased to destroy the foam which forms. The mixture assumes a greenish coloration, and it is left to reflux for 1 h. It is cooled, a solution of potassium hydrogen sulphate is added to adjust the pH to between 1 and 2, the mixture is heated to reflux for a further 1 h, then it is filtered and the filtrate is extracted with diethyl ether. After drying and evaporation of the organic phase, 72 g of crude ester are obtained, which is a mixture of ethyl 6-methoxy-3,4-dihydronaphthalene-1-acetate and of ethyl (6-methoxy-1,2,3,4-tetrahydronaphthalen-1,1-diyl)acetate.

70 g (284 mmol) of the mixture are dissolved in 500 ml of benzene, 74 g (292 mmol) of 2,3-dichloro-5,6-dicyanocyclohexa-2,5-diene-1,4-dione are added and the mixture is heated to reflux for 6 h. The mixture is filtered, the filtrate is evaporated and the residue is purified by chromatography on a silica gel column eluted with a 95:5 mixture of hexane/ethyl acetate, and 39.4 g of ester (161 mmol) are isolated.

7.2 Diethyl 2-(6-methoxynaphthalen-1-yl)propanedioate 14 g (57 mmol) of ethyl 6-methoxynaphthalene-1-acetate in solution in 46 ml of diethyl carbonate are heated to 110° C., on an oil bath, and a freshly prepared solution of sodium ethoxide (1.45 g of sodium in 30 ml of ethanol, or 63 mmol) is added, while distilling the alcohol, over 45 minutes.

The heating is maintained for 1 h, then the mixture is hydrolysed with 100 ml of water and aqueous hydrochloric acid to pH=1, and extracted twice with 150 ml of dichloromethane. After drying and evaporation of the organic phase, 20 g of crude product are obtained which is purified by chromatography on a silica gel column eluted with a mixture of hexane/diethyl ether of at first 95:5 then 80:20. 14.5 g of diester (46 mmol) are isolated.

7.3. 2-(6-Methoxynaphthalen-1-yl)propane-1,3-diol 31 g (98 mmol) of diethyl 2-(6-methoxynaphthalen-1-yl)propanedioate are dissolved in 150 ml of tetrahydrofuran, and the solution is added to 7.5 g (197 mmol) of lithium aluminium hydride suspended in 150 ml of tetrahydrofuran.

The mixture is heated to reflux for 6 h, cooled and hydrolysed while successively adding 7.5 g of water, 21 g of 10% sodium carbonate and 7.5 g of water. The mixture is stirred at about 50° C. for 1 h and filtered, while washing the solid with hot tetrahydro-furan, the filtrate is concentrated under reduced pressure, the residue taken up with chloroform, the solution washed twice with water and dried, and the solvent evaporated. The residue is purified by chromatography on a silica gel column eluted first with a 1:1 mixture of hexane/ethyl acetate, then with pure ethyl acetate. 9.5 g of diol (41 mmol) are isolated.

7.4 N-[5-(6-Methoxynaphthalen-1-yl)-1,3-dioxan-2-yl]-methylacetamide 2.3 g (10 mmol) of 2-(6-methoxynaphthalen-1-yl)propane-1,3-diol, 0.45 g of paratoluenesulphonic acid and 1.6 g (11 mmol) of N-(2,2-dimethoxyethyl)acetamide are introduced into a flask containing 200 ml of benzene.

The mixture is heated to 60° C. for 1 h, the solvent is evaporated under reduced pressure, the residue is taken up with 200 ml of benzene, the mixture is heated to 60° C. for a further 1 h and the solvent is evaporated under reduced pressure. The residue is purified by chromatography on a silica gel column eluted with a 1:1 mixture of chloroform/ethyl acetate. After recrystallisation in ethyl acetate, 1.2 g of compound (3.8 mmol) are finally isolated. Melting point: 158° C.

EXAMPLE 8

Compound No. 137

Methyl [[5-(6-methoxynaphthalen-1-yl)-1,3-dioxan-2-yl]methyl]carbamate

A mixture of 200 ml of benzene, 3 q (13 mmol) of 2-(6-methoxynaphthalen-1-yl)propane-1,3-diol, 1.5 g (14 mmol) of 2,2-dimethoxyethylamine and 50 ml of diethyl ether saturated with gaseous hydrochloric acid is heated to reflux for 3 h.

The solvents are evaporated under reduced pressure, the residue is taken up with chloroform, a solution of potassium carbonate is added, and the organic phase is separated, dried and evaporated. The residue is taken up with 100 ml of chloroform, 2.6 g (26 mmol) of triethylamine are added and then, drop by drop, 1.35 g (14 mmol) of methyl chloroformate, and the mixture is left for several hours while stirring at ambient temperature.

The organic phase is washed in an acidic medium, then in a basic medium, dried and evaporated under reduced pressure. The residual oil is purified by chromatography on a silica gel column eluted with a 99:1 mixture of chloroform/ethanol. After recrystallisation in ethyl acetate, 1.9 g of pure compound (5.7 mmol) are finally isolated.

Melting point: 142-144° C.

EXAMPLE 9

Compound No. 138

N-[3-[5-(6-Methoxynaphthalen-1-yl)-1,3-dioxan-2-yl]propyl]acetamide (of trans-diequatorial conformation)

9.1. N-(4,4-Diethoxybut-1-yl)acetamide 20 g (196 mmol) of acetic anhydride in 100 ml of benzene are added drop by drop, at reflux, to a stirred suspension of 32 g (198 mmol) of 4,4-diethoxybutylamine and 24 g (174 mmol) of potassium carbonate in 600 ml of benzene. The mixture is heated to reflux for 15 min. and cooled, the precipitate is filtered and the filtrate is evaporated to dryness. The residual oil is treated with vegetable charcoal in 300 ml of diethyl ether and, after filtration and evaporation of the filtrate in vacuo, 37.3 g of oily product are obtained. $n^{20}_D = 1.4472$.

9.2. N-[3-[5-(6-Methoxynaphthalen-1-yl)-1,3-dioxan-2-propyl]acetamide 9.5 g (41 mmol) of 2-(6-methoxynaphthalen-1-yl)propane-1,3-diol, 1 g of paratoluenesulphonic acid and 9.2 g (45 mmol) of N-(4,4-diethoxybutyl)acetamide are introduced into a flask containing 300 ml of benzene.

The mixture is stirred at 50 C for 2 h and evaporated to dryness, 300 ml of benzene are added, and the operation is repeated. 300 ml of benzene are added once more, as well as 1.4 g (7 mmol) of N-(4,4-diethoxybutyl)acetamide and the mixture is heated at 50° C. for a further 1 h.

The solvent is evaporated under reduced pressure and the residue is purified by chromatography on a silica gel column eluted with ethyl acetate. After treatment with vegetable charcoal, 11.6 g of product are obtained, which is recrystallised twice in ethyl acetate. 7.6 g of pure compound (22 mmol) are finally isolated.

Melting point: 146° C.

The table below illustrates the chemical structures and the physical properties of some compounds according to the invention. In the column "Ar", $C_6H_x$ denotes a phenyl group carrying 5-x substituents, $C_{10}H_{7-x}$-(1)- and $C_{10}H_{7-x}$-(2) denote naphthalen-1-yl and naphthalen-2-yl groups, respectively, carrying 7-x substituents, and $cC_3H_5$ denotes a cyclopropyl group.

In the column "$R_2$", $C_2H_5$, $iC_3H_7$, $iC_4H_9$ and $tC_4H_9$ denote ethyl, isopropyl, isobutyl and tertiary butyl groups respectively.

In the column "T/C", the trans/cis ratios of the compounds are indicated.

TABLE $$Ar-(CH_2)_m-\underset{O}{\overset{O}{\diagdown}}\!\!\!\diagup\!\!\!-(CH_2)_n-N\diagdown_{R_2}^{R_1}$$

| No. | Ar | m | n | $R_1$ | $R_2$ | Salt | T/C | m.p. (°C.) |
|---|---|---|---|---|---|---|---|---|
| 1 | $C_6H_5$— | 0 | 2 | $CH_3$ | $CH_3$ | HCl | 100/0 | 96–98 |
| 2 | $C_6H_5$— | 0 | 3 | H | H | HCl | 100/0 | 175–176 |
| 3 | $C_6H_5$— | 0 | 3 | H | $CH_3$ | CHl | 100/0 | 188–190 |
| 4 | $C_6H_5$— | 0 | 3 | H | $COCH_3$ | base | 100/0 | 103–104 |
| 5 | $C_6H_5$— | 0 | 3 | H | $COC_2H_5$ | base | 100/0 | 92–93 |
| 6 | $C_6H_5$— | 0 | 3 | H | $COtC_4H_9$ | base | 100/0 | 114–115 |
| 7 | $C_6H_5$— | 1 | 1 | H | $COCH_3$ | base | 55/45 | $n_D^{20}$ = 1.5280 |
| 8 | $C_6H_5$— | 1 | 2 | H | $COCH_3$ | base | 85/15 | 96 |
| 9 | $C_6H_5$— | 1 | 3 | H | $COCH_3$ | base | 60/40 | 72 |
| 10 | 2-F—$C_6H_4$— | 1 | 1 | H | $COCH_3$ | base | 60/40 | 84–86 |
| 11 | 2-F—$C_6H_4$— | 1 | 2 | H | $COCH_3$ | base | 90/10 | 94–96 |
| 12 | 2-F—$C_6H_4$— | 1 | 3 | H | $COCH_3$ | base | 90/10 | 83–85 |
| 13 | 2-F—$C_6H_4$— | 1 | 3 | H | $COOC_2H_5$ | base | 100/0 | 96–98 |
| 14 | 3-F—$C_6H_4$— | 1 | 1 | H | $COCH_3$ | base | 90/10 | 94–96 |
| 15 | 3-F—$C_6H_4$— | 1 | 2 | H | $COCH_3$ | base | 85/15 | 90–91 |
| 16 | 3-F—$C_6H_4$— | 1 | 3 | H | $COCH_3$ | base | 80/20 | 76–78 |
| 17 | 4-F—$C_6H_4$— | 0 | 1 | H | $COCH_3$ | base | 100/0 | 93–95 |
| 18 | 4-F—$C_6H_4$— | 0 | 1 | H | $COOCH_3$ | base | 100/0 | 87–89 |
| 19 | 4-F—$C_6H_4$— | 0 | 1 | $CH_3$ | $COCH_3$ | base | 75/25 | 46–48 |
| 20 | 4-F—$C_6H_4$— | 0 | 1 | $CH_3$ | $COOCH_3$ | base | 100/0 | 43–45 |
| 21 | 4-F—$C_6H_4$— | 0 | 2 | H | $COCH_3$ | base | 100/0 | 142–143 |
| 22 | 4-F—$C_6H_4$— | 0 | 2 | H | $COOCH_3$ | base | 100/0 | 92–94 |
| 23 | 4-F—$C_6H_4$— | 0 | 3 | H | $COCH_3$ | base | 100/0 | 100–102 |
| 24 | 4-F—$C_6H_4$— | 0 | 3 | H | $COOCH_3$ | base | 100/0 | 70–72 |
| 25 | 4-F—$C_6H_4$— | 1 | 1 | H | $COCH_3$ | base | 90/10 | 119–120 |
| 26 | 4-F—$C_6H_4$— | 1 | 2 | H | $COCH_3$ | base | 95/5 | 136–137 |
| 27 | 4-F—$C_6H_4$— | 1 | 3 | H | $COCH_3$ | base | 90/10 | 118–120 |
| 28 | 2-Cl—$C_6H_4$— | 0 | 1 | H | $COCH_3$ | base | 100/0 | 104–106 |
| 29 | 2-Cl—$C_6H_4$— | 0 | 2 | H | $COCH_3$ | base | 100/0 | 100–102 |
| 30 | 2-Cl—$C_6H_4$— | 0 | 3 | H | $COCH_3$ | base | 100/0 | 118–120 |
| 31 | 2-Cl—$C_6H_4$— | 1 | 1 | H | $COCH_3$ | base | 90/10 | 110–111 |
| 32 | 2-Cl—$C_6H_4$— | 1 | 2 | H | $COCH_3$ | base | 70/30 | 89–91 |
| 33 | 2-Cl—$C_6H_4$— | 1 | 3 | H | $COCH_3$ | base | 60/40 | 62–64 |
| 34 | 3-Cl—$C_6H_4$— | 0 | 1 | H | $COCH_3$ | base | 100/0 | 122–124 |
| 35 | 3-Cl—$C_6H_4$— | 0 | 1 | H | $COOCH_3$ | base | 100/0 | 72–74 |
| 36 | 3-Cl—$C_6H_4$— | 0 | 2 | H | $COCH_3$ | base | 100/0 | 112–114 |
| 37 | 3-Cl—$C_6H_4$— | 0 | 2 | H | $COOCH_3$ | base | 100/0 | 88–90 |
| 38 | 3-Cl—$C_6H_4$— | 0 | 3 | H | $COCH_3$ | base | 100/0 | 93–95 |
| 39 | 3-Cl—$C_6H_4$— | 0 | 3 | H | $COOCH_3$ | base | 100/0 | 46–48 |
| 40 | 3-Cl—$C_6H_4$— | 1 | 1 | H | $COCH_3$ | base | 90/10 | 121–122 |
| 41 | 3-Cl—$C_6H_4$— | 1 | 2 | H | $COCH_3$ | base | 80/20 | 110–111 |
| 42 | 3-Cl—$C_6H_4$— | 1 | 3 | H | $COCH_3$ | base | 85/15 | 80–82 |
| 43 | 4-Cl—$C_6H_4$— | 0 | 1 | H | H | HCl | 100/0 | 270–272 |
| 44 | 4-Cl—$C_6H_4$— | 0 | 1 | H | CHO | base | 100/0 | 112–114 |
| 45 | 4-Cl—$C_6H_4$— | 0 | 1 | H | $COCH_3$ | base | 100/0 | 112–114 |
| 46 | 4-Cl—$C_6H_4$— | 0 | 1 | H | $COOCH_3$ | base | 100/0 | 102–103 |
| 47 | 4-Cl—$C_6H_4$— | 0 | 1 | $CH_3$ | $CH_3$ | HCl | 100/0 | 238–240 |
| 48 | 4-Cl—$C_6H_4$— | 0 | 1 | $CH_3$ | $COOCH_3$ | base | 100/0 | 60–62 |
| 49 | 4-Cl—$C_6H_4$— | 0 | 2 | H | $COCH_3$ | base | 100/0 | 162–163 |
| 50 | 4-Cl—$C_6H_4$— | 0 | 2 | H | $COOCH_3$ | base | 100/0 | 118–120 |
| 51 | 4-Cl—$C_6H_4$— | 0 | 3 | H | $CH_3$ | HCl | 100/0 | 136–138 |
| 52 | 4-Cl—$C_6H_4$— | 0 | 3 | H | CHO | base | 100/0 | 114–116 |
| 53 | 4-Cl—$C_6H_4$— | 0 | 3 | H | $COCH_3$ | base | 100/0 | 103–105 |
| 54 | 4-Cl—$C_6H_4$— | 0 | 3 | H | $COOCH_3$ | base | 100/0 | 88–90 |

TABLE-continued $$Ar-(CH_2)_m-\underset{O}{\overset{O}{\diagdown}}\!\!\!\bigg\rangle\!\!\!-(CH_2)_n-N\!\!\!\diagup\!\!\!\!\overset{R_1}{\underset{R_2}{}}$$

| No. | Ar | m | n | R₁ | R₂ | Salt | T/C | m.p. (°C.) |
|---|---|---|---|---|---|---|---|---|
| 55 | 4-Cl—C₆H₄— | 0 | 3 | CH₃ | COCH₃ | base | 100/0 | 56–58 |
| 56 | 4-Cl—C₆H₄— | 0 | 4 | H | COCH₃ | base | 100/0 | 144–145 |
| 57 | 4-Cl—C₆H₄— | 0 | 4 | CH₃ | CH₃ | HCl | 100/0 | 195–196 |
| 58 | 4-Cl—C₆H₄— | 1 | 1 | H | COCH₃ | base | 60/40 | 95 |
| 59 | 4-Cl—C₆H₄— | 1 | 2 | H | COOCH₃ | base | 85/15 | 84–86 |
| 60 | 4-Cl—C₆H₄— | 1 | 3 | H | COCH₃ | base | 60/40 | 100 |
| 61 | 3,4-Cl₂—C₆H₃— | 0 | 1 | H | COCH₃ | base | 100/0 | 136–137 |
| 62 | 3,4-Cl₂—C₆H₃— | 0 | 3 | H | COCH₃ | base | 100/0 | 131–132 |
| 63 | 4-Br—C₆H₄— | 0 | 2 | H | COCH₃ | base | 100/0 | 162–163 |
| 64 | 4-Br—C₆H₄— | 0 | 3 | H | COCH₃ | base | 100/0 | 112–114 |
| 65 | 2-CH₃—C₆H₄— | 0 | 1 | H | COCH₃ | base | 100/0 | 129–130 |
| 66 | 2-CH₃—C₆H₄— | 0 | 3 | H | COCH₃ | base | 100/0 | 118–120 |
| 67 | 2-CH₃—C₆H₄— | 0 | 3 | CH₃ | COCH₃ | base | 100/0 | $n_D^{23} = 1.529$ |
| 68 | 2-CH₃—C₆H₄— | 1 | 3 | H | COCH₃ | base | 80/20 | 52–54 |
| 69 | 3-CH₃—C₆H₄— | 0 | 1 | H | COCH₃ | base | 100/0 | 120–121 |
| 70 | 3-CH₃—C₆H₄— | 0 | 3 | H | COCH₃ | base | 100/0 | 72–73 |
| 71 | 3-CH₃—C₆H₄— | 1 | 1 | H | COCH₃ | base | 90/10 | 92–93 |
| 72 | 3-CH₃—C₆H₄— | 1 | 2 | H | COCH₃ | base | 100/0 | 99–100 |
| 73 | 3-CH₃—C₆H₄— | 1 | 3 | H | COCH₃ | base | 100/0 | 86–87 |
| 74 | 4-CH₃—C₆H₄— | 0 | 1 | H | COCH₃ | base | 100/0 | 134–135 |
| 75 | 4-CH₃—C₆H₄— | 0 | 1 | CH₃ | CH₃ | HCl | 100/0 | 234–235 |
| 76 | 4-CH₃—C₆H₄— | 0 | 3 | H | COCH₃ | base | 100/0 | 124–125 |
| 77 | 4-CH₃—C₆H₄— | 1 | 1 | H | COCH₃ | base | 50/50 | 89–90 |
| 78 | 4-CH₃—C₆H₄— | 1 | 2 | H | COCH₃ | base | 100/0 | 137–138 |
| 79 | 4-CH₃—C₆H₄— | 1 | 3 | H | COCH₃ | base | 100/0 | 122–123 |
| 80 | 4-tC₄H₉—C₆H₄— | 1 | 1 | H | COCH₃ | base | 50/50 | $n_D^{26} = 1.5040$ |
| 81 | 4-tC₄H₉—C₆H₄— | 1 | 3 | H | COCH₃ | base | 60/40 | 46–48 |
| 82 | 2,3-(CH₃)₂—C₆H₃— | 1 | 1 | H | COCH₃ | base | 80/20 | 114–116 |
| 83 | 2,3-(CH₃)₂—C₆H₃— | 1 | 2 | H | COCH₃ | base | 100/0 | 120–121 |
| 84 | 2,3-(CH₃)₂—C₆H₃— | 1 | 3 | H | COCH₃ | base | 90/10 | 89–90 |
| 85 | 2,5-(CH₃)₂—C₆H₃— | 1 | 1 | H | COCH₃ | base | 100/0 | 107–108 |
| 86 | 2,5-(CH₃)₂—C₆H₃— | 1 | 1 | H | COOCH₃ | base | 100/0 | 84–85 |
| 87 | 2,5-(CH₃)₂—C₆H₃— | 1 | 2 | H | COCH₃ | base | 85/15 | 97–98 |
| 88 | 2,5-(CH₃)₂—C₆H₃— | 1 | 3 | H | COCH₃ | base | 100/0 | 95–96 |
| 89 | 2-CH₃O—C₆H₄— | 0 | 1 | H | COCH₃ | base | 90/10 | 96–98 |
| 90 | 2-CH₃O—C₆H₄— | 0 | 2 | H | COCH₃ | base | 90/10 | 88–90 |
| 91 | 2-CH₃O—C₆H₄— | 0 | 3 | H | COCH₃ | base | 100/0 | 98–100 |
| 92 | 2-CH₃O—C₆H₄— | 1 | 1 | H | COCH₃ | base | 60/40 | 82–83 |
| 93 | 2-CH₃O—C₆H₄— | 1 | 2 | H | COCH₃ | base | 90/10 | 87–89 |
| 94 | 2-CH₃O—C₆H₄— | 1 | 3 | H | COCH₃ | base | 95/5 | 96–98 |
| 95 | 3-CH₃O—C₆H₄— | 0 | 1 | H | COCH₃ | base | 90/10 | 90–92 |
| 96 | 3-CH₃O—C₆H₄— | 0 | 2 | H | COCH₃ | base | 90/10 | 88–90 |
| 97 | 3-CH₃O—C₆H₄— | 0 | 3 | H | COCH₃ | base | 85/15 | 88–90 |
| 98 | 3-CH₃O—C₆H₄— | 1 | 2 | H | COCH₃ | base | 90/10 | 108–110 |
| 99 | 3-CH₃O—C₆H₄— | 1 | 3 | H | COCH₃ | base | 75/25 | 100–102 |
| 100 | 4-CH₃O—C₆H₄— | 0 | 1 | H | H | HCl | 100/0 | 247–248 |
| 101 | 4-CH₃O—C₆H₄— | 0 | 1 | H | COCH₃ | base | 100/0 | 117.5–118 |
| 102 | 4-CH₃O—C₆H₄— | 0 | 1 | CH₃ | CH₃ | HCl | 100/0 | 210 |
| 103 | 4-CH₃O—C₆H₄— | 0 | 2 | CH₃ | CH₃ | HCl | 100/0 | 168–170 |
| 104 | 4-CH₃O—C₆H₄— | 0 | 3 | H | COCH₃ | base | 100/0 | 99–99.5 |
| 105 | 4-CH₃O—C₆H₄— | 0 | 3 | H | COC₂H₅ | base | 100/0 | 79–80 |
| 106 | 4-CH₃O—C₆H₄— | 0 | 4 | CH₃ | CH₃ | HCl | 100/0 | 175–178 |
| 107 | 4-CH₃O—C₆H₄— | 1 | 1 | H | COCH₃ | base | 90/10 | 85–86 |
| 108 | 4-CH₃O—C₆H₄— | 1 | 2 | H | COCH₃ | base | 65/35 | 89–90 |
| 109 | 4-CH₃O—C₆H₄— | 1 | 3 | H | COCH₃ | base | 50/50 | 65–66 |
| 110 | 3,4-(CH₃O)₂—C₆H₃— | 0 | 1 | H | COCH₃ | base | 100/0 | 134–136 |
| 111 | 3,4-(CH₃O)₂—C₆H₃— | 0 | 3 | H | COCH₃ | base | 100/0 | 115–116 |
| 112 | 3-CF₃—C₆H₄— | 0 | 3 | H | COCH₃ | base | 100/0 | 72–74 |
| 113 | 3-CF₃—C₆H₄— | 1 | 1 | H | COCH₃ | base | 70/30 | 117–118 |
| 114 | 3-CF₃—C₆H₄— | 1 | 1 | H | COCH₃ | base | 65/35 | 58–60 |
| 115 | 3-CF₃—C₆H₄— | 1 | 3 | H | COCH₃ | base | 100/0 | 89–90 |
| 116 | 3-CF₃-4-F—C₆H₃— | 1 | 2 | H | COCH₃ | base | 60/40 | 58–60 |
| 117 | 3-CF₃-4-F—C₆H₃— | 1 | 3 | H | COCH₃ | base | 55/45 | 39–43 |
| 118 | C₁₀H₇-(1)- | 0 | 1 | H | COCH₃ | base | 100/0 | 140–142 |
| 119 | C₁₀H₇-(1)- | 0 | 2 | H | COCH₃ | base | 80/20 | 136–139 |
| 120 | C₁₀H₇-(1)- | 0 | 3 | H | H | HCl | 100/0 | 191–192 |
| 121 | C₁₀H₇-(1)- | 0 | 3 | H | CH₃ | HCl | 100/0 | 142–144 |
| 122 | C₁₀H₇-(1)- | 0 | 3 | H | CHO | base | 100/0 | 108–110 |
| 123 | C₁₀H₇-(1)- | 0 | 3 | H | COCH₃ | base | 100/0 | 158–160 |
| 124 | C₁₀H₇-(1)- | 0 | 3 | H | COOCH₃ | base | 100/0 | 80–82 |
| 125 | C₁₀H₇-(1)- | 0 | 3 | H | COOC₂H₅ | base | 100/0 | 93–94 |
| 126 | C₁₀H₇-(1)- | 0 | 3 | H | COOiC₃H₇ | base | 100/0 | 118–120 |
| 127 | C₁₀H₇-(1)- | 0 | 3 | H | COOiC₄H₉ | base | 100/0 | 78–80 |
| 128 | C₁₀H₇-(1)- | 0 | 3 | CH₃ | COCH₃ | base | 100/0 | $n_D^{21} = 1.5752$ |
| 129 | C₁₀H₇-(1)- | 1 | 1 | H | COCH₃ | base | 60/40 | 136 |

TABLE-continued

Ar—(CH$_2$)$_m$—[1,3-dioxane]—(CH$_2$)$_n$—N(R$_1$)(R$_2$)

| No. | Ar | m | n | R$_1$ | R$_2$ | Salt | T/C | m.p. (°C.) |
|---|---|---|---|---|---|---|---|---|
| 130 | C$_{10}$H$_7$-(1)- | 1 | 2 | H | COOCH$_3$ | base | 100/0 | 86 |
| 131 | C$_{10}$H$_7$-(1)- | 1 | 3 | H | COCH$_3$ | base | 60/40 | 105 |
| 132 | 4-Cl—C$_{10}$H$_6$-(1)- | 0 | 1 | H | COCH$_3$ | base | 100/0 | 188–190 |
| 133 | 4-Cl—C$_{10}$H$_6$-(1)- | 0 | 3 | H | COCH$_3$ | base | 100/0 | 140–142 |
| 134 | 6-Cl—C$_{10}$H$_6$-(1)- | 0 | 1 | H | COCH$_3$ | base | 100/0 | 166–168 |
| 135 | 6-Cl—C$_{10}$H$_6$-(1)- | 0 | 3 | H | COCH$_3$ | base | 100/0 | 160–162 |
| 136 | 6-CH$_3$O—C$_{10}$H$_6$-(1)- | 0 | 1 | H | COCH$_3$ | base | 100/0 | 158 |
| 137 | 6-CH$_3$O—C$_{10}$H$_6$-(1)- | 0 | 1 | H | COOCH$_3$ | base | 100/0 | 142–144 |
| 138 | 6-CH$_3$O—C$_{10}$H$_6$-(1)- | 0 | 3 | H | COCH$_3$ | base | 100/0 | 146 |
| 139 | 7-CH$_3$O—C$_{10}$H$_6$-(1)- | 0 | 1 | H | COCH$_3$ | base | 90/10 | 138–140 |
| 140 | 7-CH$_3$O—C$_{10}$H$_6$-(1)- | 0 | 3 | H | COCH$_3$ | base | 100/0 | 132–134 |
| 141 | 6-cC$_3$H$_5$CH$_2$O—C$_{10}$H$_6$-(1)- | 0 | 3 | H | COCH$_3$ | base | 90/10 | 124–126 |
| 142 | C$_{10}$H$_7$-(2)- | 0 | 1 | H | COCH$_3$ | base | 100/0 | 138–140 |
| 143 | C$_{10}$H$_7$-(2)- | 0 | 3 | H | COCH$_3$ | base | 100/0 | 135–136 |
| 144 | C$_{10}$H$_7$-(2)- | 1 | 1 | H | COCH$_3$ | base | 60/40 | 116 |
| 145 | C$_{10}$H$_7$-(2)- | 1 | 3 | H | COCH$_3$ | base | 100/0 | 106 |
| 146 | 6-CH$_3$—C$_{10}$H$_6$-(2)- | 0 | 1 | H | COCH$_3$ | base | 100/0 | 180–182 |
| 147 | 6-CH$_3$—C$_{10}$H$_6$-(2)- | 0 | 3 | H | COCH$_3$ | base | 85/15 | 140–142 |
| 148 | 6-CH$_3$O—C$_{10}$H$_6$-(2)- | 0 | 1 | H | COCH$_3$ | base | 90/10 | 132–134 |
| 149 | 6-CH$_3$O—C$_{10}$H$_6$-(2)- | 0 | 3 | H | COCH$_3$ | base | 95/5 | 126–128 |
| 150 | 6-cC$_3$H$_5$CH$_2$O—C$_{10}$H$_6$-(2)- | 0 | 3 | H | COCH$_3$ | base | 100/0 | 118–120 |

The compounds of the invention have been the subject of pharmacological tests which have demonstrated their therapeutic properties.

In these tests, their potential anticonvulsive activity has been tested in different experimental models in the mouse (convulsions caused by maximal electroshock and mortality induced either by bicuculline, or by strychnine), according to the protocols described by E. A. Swinyard and J. H. Woodhead in "Experimental detection, quantification and evaluation of anticonvulsants" (Antiepileptic Drugs, D. M. Woodbury, J. K. Penry and C. E. Pippenger (Eds), Raven Press, New York, pp. 111–125 (1982)).

In these models, the most active compounds have an AD$_{50}$ (active dose which inhibits 50% of the convulsions or the mortality induced by the different convulsive agents) of the order of 20 mg/kg when administered intraperitoneally and of the order of 40 mg/kg when administered orally.

The compounds have likewise been the subject of another test, described by C. Fleury in "Nouvelle technique pour mesurer l'effort musculaire de la souris, dite test de l'agrippement" [Novel technique for measuring the muscular effort of the mouse, called the gripping test], (Arch. Sci. (Geneva), 10, 107–113 (1957)). The most active compounds in this test have no effect at the maximum tested dose of 600 mg/kg when administered orally.

Finally, another test, called the rota rod test, described by N. W. Dunham and T. S. Miya in "A note on a simple apparatus for detecting neurological deficit in rats and mice", (J. Am. Pharm. Assoc., 46, 208–209 (1957)), has shown that the compounds of the invention do not present any neurotoxic signs at the maximum tested dose of 400 mg/kg when administered orally.

The results of the tests show that, through their anticonvulsive properties, the compounds of the invention could be used for the treatment of epilepsy. The treatment of other ailments, such as spasticity, dyskinesias, depression, can likewise be envisaged.

For this purpose, they can be formulated as pharmaceutical compositions in which they are the active ingredient. They can be presented in all pharmaceutical forms permitting their enteral or parenteral administration, in association with appropriate excipients, such as tablets, coated tablets, capsules including hard gelatin capsules, suppositories, drinkable or injectable solutions and suspensions, divided into doses permitting a dosage of 5 to 15 mg/kg of active substance per day.

We claim:

1. A compound which is a 2-aminoalkyl-5-arylalkyl-1,3-dioxane of general formula (I)

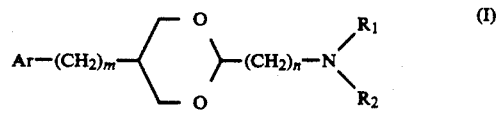

in which
m represents 0 or 1;
n represents 1, 2, 3 or 4;
R$_1$ represents hydrogen or methyl;
R$_2$ represents hydrogen, methyl or an alkanoyl group of the general formula COR' in which R' represents a hydrogen atom or a linear or branched C$_1$-C$_4$-alkyl group, or an alkoxycarbonyl group of the general formula COOR" in which R" represents a linear or branched C$_1$-C$_4$-alkyl group; and
Ar represents either a phenyl group optionally carrying one or two substituents selected from halogen, C$_1$-C$_4$ alkyl, methoxy and trifluoromethyl, or a naphthalen-1-yl or naphthalen-2-yl group optionally carrying a substituent selected from halogen, methyl, methoxy and cyclopropylmethoxy groups, in the form of a cis- or trans-stereoisomer, and in the form of a free base or a acid addition salt thereof.

2. A compound according to claim 1, wherein Ar represents an optionally substituted naphthalen-1-yl or naphthalen-2-yl group.

3. A compound according to claim 1, wherein Ar is chlorophenyl, naphthalen-1-yl optionally substituted with methoxy; n is 1 or 3; and any acid addition salt is the hydrochloride.

4. A compound according to claim 1, which is N-[3-[5-(naphthalen-1-yl)-1,3-dioxan-2-yl]propyl]-acetamide.

5. A compound according to claim 1, which is N-[3-[5-(6-methoxynaphthalen-1-yl)-1,3-dioxan-2-yl]propyl]acetamide.

6. A pharmaceutical composition, comprising as active ingredient an effective amount of a compound as claimed in claim 1 associated with a pharmaceutical excipient.

7. A method of treating epilepsy, which comprises administering to a thus-afflicted patient an effective amount of a compound as claimed in claim 1.

8. A method of treating a patient afflicted with or subject to convulsions, which comprises administering to the patient an effective amount of a compound as claimed in claim 1.

* * * * *